US005361304A

United States Patent [19]

Jones et al.

[11] Patent Number: 5,361,304

[45] Date of Patent: Nov. 1, 1994

[54] HEADPHONE ASSEMBLIES

[75] Inventors: Owen Jones; Michael C. J. Trinder, both of Colchester, England

[73] Assignee: University of Essex, England

[21] Appl. No.: 565,434

[22] Filed: Aug. 10, 1990

Related U.S. Application Data

[63] Continuation-in-part of Ser. No. 323,586, Mar. 14, 1989, abandoned.

[51] Int. Cl.[5] ........................ A61F 11/02; G10K 11/16

[52] U.S. Cl. ........................ 381/72; 381/195; 381/71

[58] Field of Search ................. 381/195, 196, 203, 72, 381/71

[56] References Cited

U.S. PATENT DOCUMENTS

| | | | |
|---|---|---|---|
| 3,873,784 | 3/1975 | Doschek | 381/203 |
| 4,833,719 | 5/1989 | Carme et al. | 381/72 |
| 4,953,217 | 8/1990 | Twiney et al. | 381/72 |
| 5,003,609 | 3/1991 | Muraoka | 381/195 |

OTHER PUBLICATIONS

Advertisement for Yamaha YH-1/2/3 Orthodynamic Headphone, Apr. 1983.

*Primary Examiner*—Forester W. Isen
*Attorney, Agent, or Firm*—Weingram & Zall

[57] ABSTRACT

A headphone assembly for an active noise cancellation system has a rigid moulded plastics shell having a rigid baffle dividing the shell interior into a front volume and a closed rear volume, both of which may be filled with an acoustic foam. The baffle has a central opening in which is mounted a headphone transducer, and a seal cushion is disposed around the mouth of the shell, to effect an air-tight seal against the user's head. The headphone transducer has two effective sound radiating surfaces of different sizes, and may be constructed as a form of orthodynamic drive unit. In the latter case, the orthodynamic drive unit diaphragm may have two separate coils of different radial extents.

11 Claims, 3 Drawing Sheets

(A) (B)

HEADPHONE ASSEMBLIES

CROSS-REFERENCE TO RELATED APPLICATIONS

This application is a continuation-in-part of our prior U.S. patent application Ser. No. 07/323,586, filed 14, Mar. 1989 and claiming the priority of UK Patent Application No. 88 06243 filed Mar. 16, 1988.

BACKGROUND OF THE INVENTION a) Field of the Invention

This invention relates to headphone units for use in active ear defender systems, as well as to headphone assemblies incorporating such headphone units and to active ear defender systems incorporating such headphone assemblies.

b) Description of the Prior Art

It is known to protect the ears of a person working in a noisy environment using a so-called active ear defender system, wherein the person wears a headphone assembly the drive units of which are driven with an electrical signal which is controlled to reduce to a minimum the instantaneous sound pressure within the cavity between the person's ear and the headphone drive unit. This is achieved by providing a microphone within that cavity, the microphone serving to sense the instantaneous sound pressure level within the cavity, the microphone output being used to control the electrical signal supplied to the headphone drive unit. Phase control of the headphone drive unit is most important, to prevent the system becoming unstable, and to this end the microphone is usually placed close to the drive unit, the physical size of which is maintained relatively small.

A known form of headphone for use in an active ear defender system as described above is disclosed in U.S. Pat. No. 4,644,581 (Bose Corporation). The headphone unit described in that Specification employs a drive unit of 23 mm diameter, and sound pressure levels in the headphone cavity of 125 dB at 300 Hz and 115 dB at 20 Hz can be achieved. However, field trials in various noisy areas have shown that the noise spectrum may extend over a greater frequency range, and that sound pressure levels as high as 140 dB are not uncommon, within the frequency range from 20 to 150 Hz. On account of the limited size of the drive unit in the arrangement of the U.S. Patent Specification referred to above, the headphone cannot be used to achieve sufficient sound pressure levels to give adequate defence against such noisy environments, especially if the frequency range is somewhat extended. Higher sound pressure levels could be achieved by reducing the volume between the drive unit and the ear cavity of the user, but then the passive performance of the headphone unit would suffer unacceptably.

OBJECTS OF THE INVENTION

The present invention stems from research into improvements in headphone assemblies such as those described in U.S. Pat. No. 4,644,581. It is thus a principal object of the present invention to extend the frequency range over which an active ear defender system incorporating such a headphone may operate, as well as to increase the power output of the headphone to permit the cancellation of even greater sound pressure levels.

A further object of this invention is to provide a headphone unit for an ear defender system, in which a good passive performance is maintained, whilst still permitting an enhanced active performance especially at lower frequencies.

Yet another object is to provide a headphone unit which is of relatively low weight and simple construction but which still gives an excellent performance.

Another object of this invent ion is to provide an improved drive unit for an active ear defender headphone assembly wherein phase errors may be minimised, whilst still permitting use over an extended frequency range.

A further object of this invention is the provision of a modified form of orthodynamic headphone drive unit, able to give high output levels over an extended frequency range.

SUMMARY OF THE INVENTION

According to one aspect of the present invention, there is provided a headphone unit for use in an active ear defender system, which headphone unit comprises a shell having a mouth adapted to fit over the ear of a user, and sealing means disposed around the mouth the shell for sealing against the head of a user to minimise air leakage when the headphone unit is in use, between the ambient and the interior of said shell. A headphone transducer is mounted within the shell, and so is a microphone to sense the acoustic output from the headphone transducer, thereby to detect the instantaneous sound pressure level within said shell. The headphone transducer has at least two effective sound radiating surfaces of different sizes and the microphone is positioned to sense the acoustic outputs from both sound radiating surfaces of the transducer.

Another aspect of the present invention provides an orthodynamic drive unit for use in a headphone assembly, which orthodynamic drive unit includes a pair of magnets between which is mounted a highly flexible diaphragm, and first and second generally-spirally wound drive coils formed substantially co-axially on the diaphragm, the first drive coil having a smaller radial extent than the second drive coil.

Yet another aspect of the present invention comprises an orthodynamic drive unit as described above in combination with a substantially rigid headphone shell having a mouth and adapted to fit over the ear of a user and sealing means disposed around the mouth of said shell for sealing against the head of a user to minimise air leakage when the headphone is in use, between the ambient and the interior of said shell. A substantially rigid baffle is provided within and connected to the shell to divide the interior of said shell into an open front volume and a closed rear volume, there being an opening in said baffle in which is mounted the orthodynamic drive unit. A microphone is also mounted within the shell to sense the instantaneous sound pressure in front of the transducer.

These aspects of this invention will now be described in greater detail and certain specific embodiments thereof set out, in order that this invention may better be understood.

BRIEF DESCRIPTION OF THE DRAWINGS

In the accompanying drawings, there are illustrated certain specific embodiments of this invention, to be described below.

In the drawings.

DESCRIPTION OF THE PREFERRED EMBODIMENTS

Figure 1:
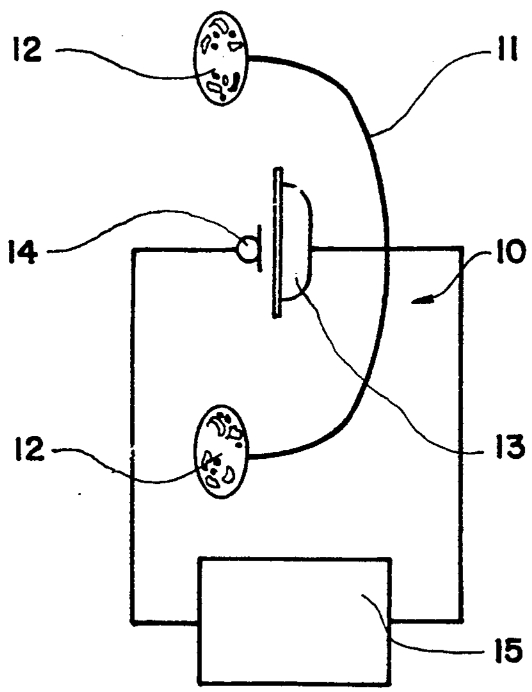
FIG. 1 is a diagrammatic view of an active noise cancellation system employing a headphone assembly.

In order to obtain increased sound pressure levels, the volume of air which is moved by the transducer must be increased. This may be achieved either by increasing the excursion (i.e. the axial movement) of the diaphragm of the transducer, or by increasing the diameter of the transducer diaphragm, or by a combination of these. The excursion of the diaphragm of a relatively small diameter transducer (such as is discussed in U.S. Pat. No. 4,664,581) inevitably is limited by the physical constraints imposed by the small size of the transducer. Such constraints include non-linearity effects at the limits of the excursion, the dissipation of heat and the provision of a sufficiently high magnetic flux density in the region of the transducer coil.

An advantage stemming from the use of a larger drive unit is that it allows the selection of appropriate front and rear volumes to optimise the passive performance of the headphone unit, in view of the greater sound pressure levels which can be achieved with such a unit. On the other hand, with an increased diameter transducer, problems arise in the positioning of the microphone to permit the sensing of the instantaneous sound pressure level within the cavity between the transducer and the user's ear. Presuming the microphone is mounted on-axis and relatively close to the transducer diaphragm (to minimise phase errors), the respective path lengths from the microphone to the central and peripheral regions of the diaphragm are significantly different, leading to different propagation times for wave fronts generated by the diaphragm. This time difference is not greatly significant at low frequencies, but at higher frequencies can become comparable to the period of the sound frequency at which cancellation is required. Since the phase of the sound pressure generated by the transducer is critical to ensure satisfactory noise cancellation and stability, increasing the diaphragm diameter decreases the useful frequency range, if instability is to be avoided. The present invention has addressed this problem, and has solved it by providing a headphone drive unit having at least two effective sound radiating surfaces.

The use of two effective sound radiating surfaces gives rise to one of two advantages: either the headphone unit may be used to operate over substantially the same frequency range as a single sound radiating surface headphone unit, but with much simpler control electronics, or the headphone unit may be used with a much extended frequency range for effective noise reduction.

The control electronics of an active ear defender system incorporating a headphone unit as described above should be arranged to feed the lower frequencies of the sound spectrum to the larger sound radiating surface and to feed the higher frequencies to the smaller sound radiating surface. In this way, the propagation times from the sound radiating surfaces to the microphone may be control led by suitable juxtapositioning of those surfaces and the microphone, so as to minimise phase errors in the overall noise cancellation system.

Most preferably, the two sound radiating surfaces are arranged co-axially, with the microphone disposed on the same axis immediately adjacent the sound radiating surfaces. Most preferably, each sound radiating surface has its own drive coil which is driven through a suitable cross-over arrangement from an amplifier controlled by the microphone, the cross-over arrangement being similar to that commonly employed with multiple drive unit loud-speakers for the high fidelity reproduction of sound. It will however be appreciated that by the arrangement of this invention, far greater sound levels may be achieved over a much greater frequency range than would be the case were a single sound radiating surface be used, such as is described in U.S. Pat. No. 4,664,581.

An orthodynamic drive unit may be employed in a headphone unit according to this aspect of the present invention with great advantage, for we have established such an orthodynamic drive unit may be modified so as to provide two effective sound radiating surfaces. If this be done, then the effective frequency range as well as the achievable sound pressure levels may significantly be extended, so leading to an even better performance for noise cancellation, whilst minimising the likelihood of instability. The modification of the orthodynamic drive unit in accordance with a further aspect of this invention concerns providing two drive coils on the diaphragm of the drive unit, the first coil being located essentially in the central region of the diaphragm and the second coil having a significantly greater radial extent, out towards the periphery of the diaphragm. The higher frequency components of the drive signal may then be supplied to the first drive coil and the lower frequency components to the second drive coil and optionally also to the first drive coil. Provided that the microphone of the headphone unit is disposed relatively close to and substantially co-axial with the orthodynamic drive unit, the path length from all portions of the orthodynamic drive unit which radiate the high frequency sounds will be relatively short, so minimising phase errors and assisting the maintenance of stability.

The modified form of orthodynamic drive unit of this invention as described above may have the second coil disposed wholly beyond the radial limit of the first coil, or the second coil may be formed so as to have a portion which extends over the same area as the first drive coil. This may be done by having the inner spiral turns of the second drive coil interfitting with the spiral turns of the first coil. If then the radially inner ends of the drive coils are commoned, only three separate connections need be made to the diaphragm, one to the common central point as well as to the two outer ends of the first and second coils.

The shell and baffle of the headphone unit of this invention may be substantially rigid with the headphone transducer mounted on that baffle: it is then found that better performance may be obtained especially at lower frequencies. In part this is because the substantially rigid shell and baffle improve the passive performance, with the shell assisting attenuation of the ambient sound pressure levels. The attenuation of the ambient sound pressure levels may be increased by substantially filling the rear volume (i.e. the closed volume between the baffle and the back of the shell) with an acoustic foam. This effect may further be enhanced by at least partially filling the front volume of the headphone unit with an acoustic foam. This foam in the front volume may leave clear a passageway substantially co-axial with the transducer, in which passageway may be provided the microphone. The use of foam in the front volume dampens resonances, but also makes the headphone unit less user-specific, giving a more uniform performance from one user to another.

A significant advantage obtained by the headphone unit as described above is that the overall mass of the headphone unit may be maintained at a relatively low level, in view of the unitary moulding of the shell and baffle. This may be compared to the expected mass, were a conventional passive ear defender modified by adding thereto an active noise reduction system.

The control electronics used with a headphone unit of this invention to complete an active noise reduction system should be designed to optimise the performance of the system, as a whole. The bandwidth of cancellation of a single headphone drive unit is typically over 6 octaves. A shallow roll-off at high frequencies of the open loop transfer function is preferred so as to broaden the enhancement, which is inherent in any system of this type, over a wide band but of a low amplitude. The open loop transfer function with this characteristic is less sensitive to component tolerances and variations between users caused by the differing placements on the head each time the ear defenders are used. Separately, when optimum cancellation performance is required for each ear defender, automatic gain control can be incorporated.

Electronic circuit topology can be used to by-pass the contribution of the acoustical path of the active noise reduction system at high frequencies, thereby making the control loop less sensitive to acoustic delays.

The electrical power for the circuitry and headphone may be derived from an electrical cable harness, as is known for use in communication headsets, or from batteries. In the latter case, the batteries can be housed together with the electronic circuitry in the ear defender shell.

This invention extends to a headphone assembly comprising a pair of headphone units of this invention as described above together with a suitable head-band therefor. The invention further extends to an active ear defender system whenever incorporating one or more headphone units of this invention as described above.

The drawings accompanying this Specification will now be described in detail, in order further to explain preferred features of headphone units of this invention. Referring initially to FIG. 1, there is shown an active noise cancellation system in diagrammatic form. This system includes a headphone unit 10 comprising a shell 11 and a seal cushion 12 around the mouth of the shell, a headphone transducer (drive unit) 13 being mounted within the shell as well as a microphone 14, disposed closely adjacent the transducer 13. The headphone transducer 13 is driven by an electrical signal provided by an electronic control circuit 15, the output of the microphone being provided to that circuit 15 to control the signal provided to the headphone transducer 13 in such a manner that the headphone transducer provides an output which minimises the sound pressure level in the region of the microphone. It will be appreciated that for this purpose, phase stability is most important; should phase errors occur, the active noise reduction system rapidly will become unstable.

Figure 2:
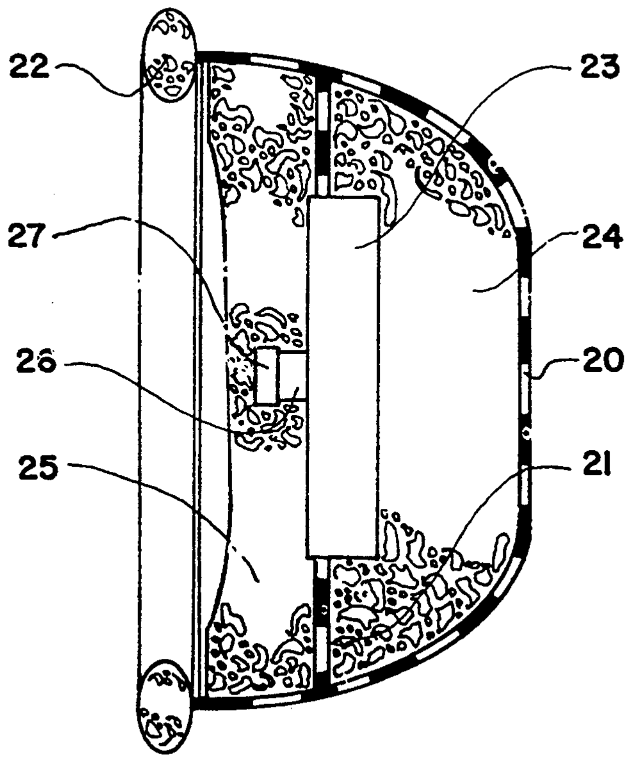
FIG. 2 is a cross-sectional view through a headphone unit of this invention.
Figure 3:
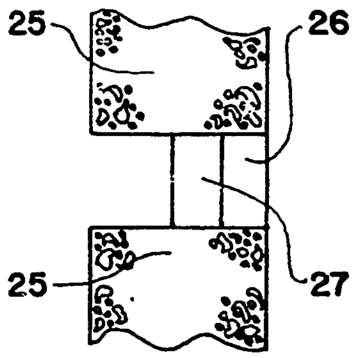
FIG. 3 is a detail view on part of the headphone unit of FIG. 1.

FIGS. 2 and 3 show a first specific embodiment of headphone unit of this invention. This headphone unit comprises a substantially rigid cup-shaped shell 20, within which is mounted a substantially rigid baffle 21. Around the mouth of the shell 20 there is provided a resilient cushion-like seal member 22, which seal member is adapted to minimise air leakage between the interior of the shell 20 and the head of a user, when the headphone is being worn over an ear.

The baffle 21 has a central opening in which is mounted a headphone transducer 23. The volume behind that transducer, between the baffle 21 and the shell, is closed and is filled with an open cell acoustic foam 24: a similar open cell acoustic foam 25 is provided within the front part of the shell, between the baffle 21 and the seal member 22. However, a central passageway 26 is foraged in that acoustic foam, and in that passageway 26 there is mounted a microphone 27.

It will be appreciated that the construction described above has a closed rear volume behind the headphone transducer, and when the headphone unit is being worn, a substantially closed front volume is formed between the transducer and the head of a user. The open cell acoustic foam serves to dampen resonances and to provide sound absorption.

The headphone transducer may take any one of a number of different forms. Conventional moving coil devices are readily available with diaphragm diameters of 40 to 50 mm and these may be adequate to generate the desired cancellation of a noise sound-wave, depending upon the intensity and spectrum of that noise. For specific applications, the acoustic or mechanical impedance of the headphone transducer could be designed to resonate in order to enhance the headphone unit sensitivity over the desired frequency range of cancellation, trading off bandwidth for increased sensitivity. The amplitude/frequency response of the headphone transducer does not have to be flat over the required frequency range, as an uneven response can be tolerated or even compensated for, in the electronic control circuit. A roll-off at higher frequencies is an advantage for noise cancellation systems, in order to improve stability.

Figure 4:
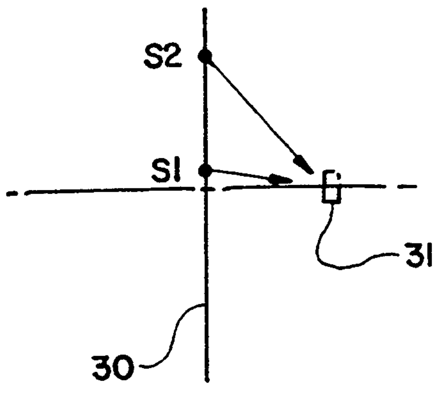
FIG. 4 illustrates the path-lengths from the diaphragm of a headphone transducer to a microphone.

As will be appreciated from FIG. 4, if the diameter of the diaphragm 30 of a transducer is increased, the path length from a peripheral region S1 of the diaphragm to a microphone 31 mounted adjacent the diaphragm central region will be increased. The contribution from the pressure elemental source S1 will arrive at the microphone 31 later than the contribution of the central elemental source S2, and associated with an increase in distance is a group delay of the sound-wave. For low frequencies the difference in distance of the pressure elemental contributions S1 and S2 is extremely small compared with the wavelength of the sound and the group delay is relatively insignificant. However, for increasing frequencies the group delay becomes more appreciable and limits the frequency range for the cancellation.

Figure 5:
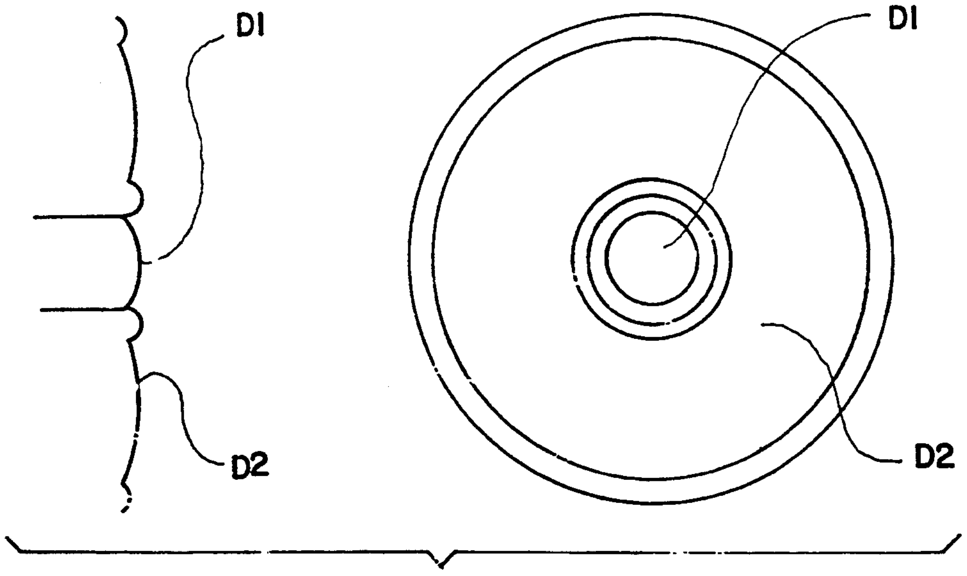
FIGS. 5A and 5B illustrate a modified form of transducer for use in a headphone unit of this invention.

FIGS. 5A and 5B show a modified form of moving coil transducer diaphragm, specifically arranged to have two sound radiating surfaces in an attempt to overcome the above problem. The diaphragm is formed in two concentric portions D1 and D2, with a resilient mechanical decoupling ring disposed therebetween.

The drive coil is connected to the central portion in a manner known in the art: the higher frequencies will then be radiated from the central portion D1 though the lower frequencies will be radiated by both portions D1 and D2.

Figure 6:
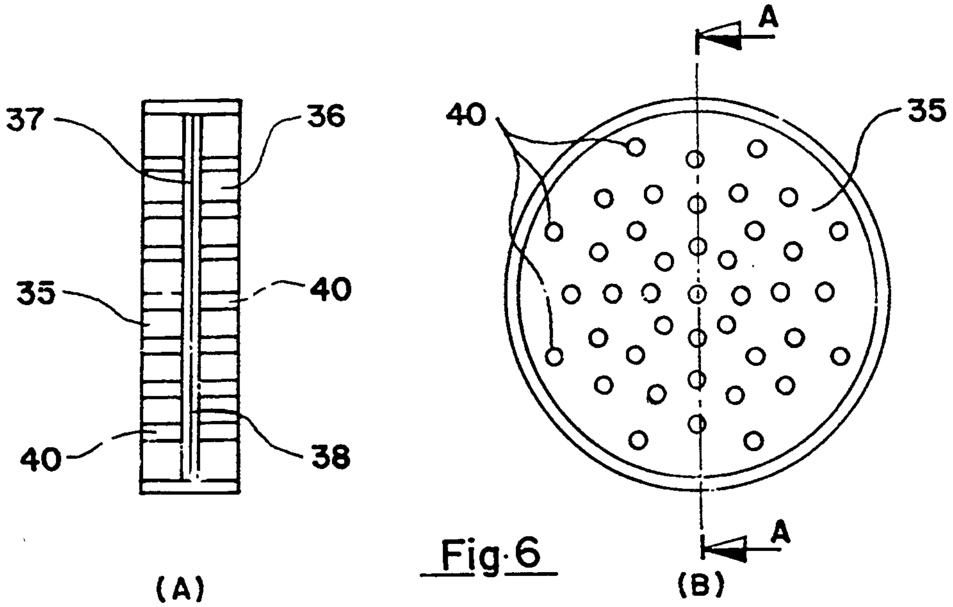
FIGS. 6A and 6B are respectively front and cross-sectional views through an orthodynamic drive unit.
Figure 7:
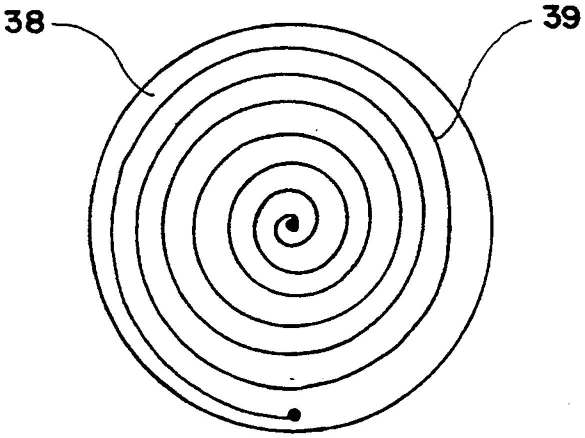
FIG. 7 is a plan view of the diaphragm of the orthodynamic drive unit of FIGS. 6A and 6B.

The transducer used in the headphone unit of this invention may comprise an orthodynamic transducer, such as is illustrated in FIGS. 6 and 7. This transducer comprises a pair of disc magnets 35 and 36 mounted so as to lie parallel to each other with a relatively narrow gap 37 therebetween, a diaphragm 38 made from a relatively thin sheet of a highly flexible plastics material being clamped to lie within that gap 37. The diaphragm 38 has formed thereon a spiral coil 39, extending from the central region of the diaphragm spirally towards the periphery. Electrical connections (not shown) are made to the two ends of the spiral coil. The magnets 35 and 36 are provided with holes 40 to permit the sound generated by the diaphragm to leave the gap between the magnets.

It will be appreciated that an orthodynamic transducer as described above has a diaphragm 38 which is driven substantially uniformly over the entire area of the diaphragm, rather than just from the central region thereof, as in the case of a conventional moving coil transducer. This arrangement allows very high sound pressure levels to be generated with excellent phase linearity.

Figure 8:
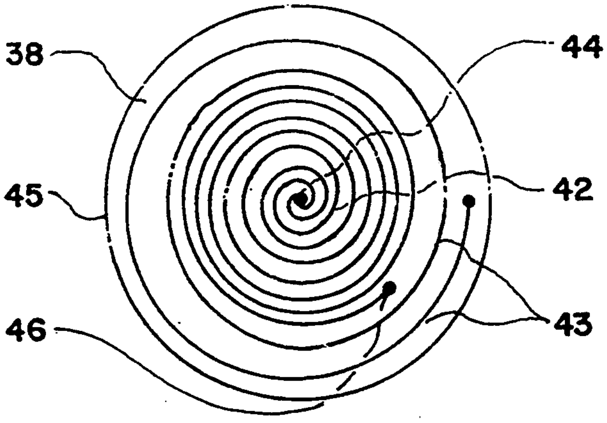
FIG. 8 is a plan view of a modified form of orthodynamic drive unit.

The orthodynamic drive unit described above may be provided with modified diaphragm, as illustrated in FIG. 8, so as to provide two distinct sound radiating surfaces. A second coil 42 is provided spirally in the central region of the diaphragm, with the turns of that second coil being interleaved with the turns of the first coil 43. The inner ends of both coils are connected together at the centre 44 of the diaphragm and a single electrical connection may be made thereto; further electrical connections may be made to the radially outer ends 45 and 46 of the two coils, so that separate electrical drive signals may be supplied to the two coils. By driving the smaller diameter coil only with the high frequency components, the central region of the diaphragm may serve to generate the higher frequency components of the sound spectrum, with the lower frequency components being generated solely by the larger diameter coil. This may be achieved using a cross-over arrangement in conjunction with the electronic control circuit providing the drive current for the transducer.

We claim:

1. A headphone unit for use in an active ear defender system, which headphone unit comprises a shell having a mouth configured to fit over the ear of a user, sealing means disposed around the mouth of the shell for sealing against the head of a user to minimize air leakage when in use between the ambient and the interior of the shell, a headphone transducer mounted within the shell, and a microphone disposed within the shell to sense the acoustic output from the headphone transducer to detect the instantaneous sound pressure level within the shell, said headphone transducer having a single diaphragm, two independently fed coils being provided on said diaphragm to define at least two effective sound radiating surfaces of different sizes said coils being arranged to be independently fed with drive current and the microphone being positioned to sense the acoustic outputs from both sound radiating surfaces of the transducer.

2. A headphone unit for use in an active ear defender system, which headphone unit comprises a shell having a mouth configured to fit over the ear of a user, sealing means disposed around the mouth of the shell for sealing against the head of a user to minimize air leakage when in use between the ambient and the interior of the shell, a headphone transducer mounted within the shell, and a microphone disposed within the shell to sense the acoustic output from the headphone transducer to detect the instantaneous sound pressure level within the shell, said headphone transducer having at least two effective sound radiating surfaces of different sizes and arranged co-axially, each sound radiating surface having an individual drive coil arranged for the separate supply of drive current thereto, and the microphone being positioned to sense the acoustic outputs from both sound radiating surfaces of the transducer.

3. A headphone unit according to claim 2, wherein one of the two sound radiating surfaces co-axially surrounds the other of said two surfaces, a resilient mechanical decoupling ring being disposed between the two sound radiating surfaces.

4. A headphone unit according to claim 2, wherein the headphone transducer comprises a pair of magnets mounted with a substantially parallel gap therebetween, a highly flexible diaphragm being mounted in the gap, and there being first and second generally-spirally wound drive coils formed on the diaphragm, the first drive coil defining one of said two sound radiating surfaces and the second drive coil defining the other of said sound radiating surfaces and the first drive coil having a smaller radial extent than the second drive coil.

5. A headphone unit according to claim 4, wherein the second drive coil is disposed wholly beyond the radial limit of the first drive coil.

6. A headphone unit according to claim 4, wherein the second drive coil has a portion which extends over the same area of the diaphragm as the first drive coil.

7. A headphone unit according to claim 2, wherein the shell is substantially rigid and a substantially rigid baffle is provided within and connected to the shell to divide the interior of the shell into an open front volume in the region of the mouth of the shell and a closed rear volume, the headphone transducer being mounted in an opening in the baffle.

8. A headphone unit according to claim 7, wherein at least one of the closed rear volume and the open front volume is substantially filled with an acoustic foam.

9. A headphone unit for use in an active ear defender system, which headphone unit comprises a substantially rigid shell having a mouth adapted to fit over the ear of a user, sealing means disposed around the mouth of said shell for sealing against the head of a user to minimize air leakage when in use between the ambient and the interior of said shell, a substantially rigid baffle provided within and connected to said shell to divide the interior thereof into an open front volume and a closed rear volume, an opening being formed in said baffle, a headphone transducer mounted within said opening in the baffle, a microphone disposed within the front volume of the shell to sense the acoustic output from the headphone transducer to detect the instantaneous sound pressure level within said shell, and at least one of said front and rear volumes being substantially filled with an acoustic foam, said headphone transducer having a single diaphragm, two independently fed coils being provided on said diaphragm to define at least two effective sound radiating surfaces of different sizes said coils being arranged to be independently fed with drive current and the microphone being positioned to sense the acoustic outputs from both sound radiating surfaces of the transducer.

10. A headphone assembly comprising in combination an orthodynamic drive unit and a substantially rigid headphone shell having a mouth adapted to fit over the ear of a user, wherein said orthodynamic drive unit comprises a pair of magnets mounted with a substantially parallel gap therebetween, a highly flexible diaphragm mounted in said gap, and first and second generally-spirally wound drive coils formed on said diaphragm, the first drive coil having a smaller radial extent than the second drive coil, the first and second drive coils being independently fed and forming at least two effective sound radiating surfaces of different sizes, and wherein there is sealing means disposed around the mouth of said shell for sealing against the head of a user to minimize air leakage when in use between the ambient and the interior of said shell, a substantially rigid baffle provided within and connected to the shell to divide the interior of said shell into an open front volume and a closed rear volume, an opening in said baffle in which is mounted said orthodynamic drive unit, and a microphone mounted within the shell to sense the instantaneous sound pressure in front of the transducer.

11. A headphone unit according to claim 10, in which at least one of said closed rear volume and said front volume is substantially filled with an acoustic foam.

* * * * *